United States Patent [19]

Shelley

[11] Patent Number: 5,145,641
[45] Date of Patent: Sep. 8, 1992

[54] AUTOCLAVES

[75] Inventor: Richard M. Shelley, Pontypridd, Wales

[73] Assignee: Smiths Industries Public Limited Company, London, England

[21] Appl. No.: 600,698

[22] Filed: Oct. 22, 1990

[30] Foreign Application Priority Data

Oct. 20, 1989 [GB] United Kingdom ............... 8923673

[51] Int. Cl.⁵ ............................................. A61L 2/06
[52] U.S. Cl. ..................................... 422/26; 422/106; 422/295; 422/298
[58] Field of Search .................. 422/26, 106, 295, 298, 422/107, 116; 73/304 R

[56] References Cited

U.S. PATENT DOCUMENTS

| | | | |
|---|---|---|---|
| 2,848,666 | 8/1958 | Zito | 422/106 |
| 3,574,529 | 4/1971 | Larro | 422/106 |
| 3,584,643 | 6/1971 | Burke | 73/304 R |
| 3,657,556 | 4/1972 | Foster | 73/304 R |
| 3,905,243 | 9/1975 | Goldfuss | 73/295 |
| 3,967,494 | 7/1976 | Joslyn | 422/26 |
| 4,125,021 | 11/1978 | Kamei et al. | 73/304 R |
| 4,781,898 | 11/1988 | Jones | 422/295 |
| 4,865,814 | 9/1989 | Childress | 422/116 |
| 4,891,188 | 1/1990 | Albright et al. | 422/26 |

FOREIGN PATENT DOCUMENTS

| | | | |
|---|---|---|---|
| 3025982 | 1/1982 | Fed. Rep. of Germany | 422/106 |
| 970055 | 9/1964 | United Kingdom . | |
| 1235952 | 6/1971 | United Kingdom . | |
| 1284767 | 8/1972 | United Kingdom . | |
| 2178961 | 2/1987 | United Kingdom . | |
| 88/06458 | 9/1988 | World Int. Prop. O. . | |

Primary Examiner—Lynn M. Kummert
Assistant Examiner—Krisanne M. Thornton
Attorney, Agent, or Firm—Pollock, VandeSande and Priddy

[57] ABSTRACT

An autoclave has a water level sensor in a water reservoir in the pressure vessel. An external water tank is connected to the reservoir via an electrically-operated valve. An electrical resistance heating element in the reservoir heats the sensor if it indicates a full level at the start of operation, in order to dry any exposed part of the sensor and thereby prevent an erroneous output from the sensor caused by water clinging to it. This heating of the sensor can be repeated if it continues to indicate a full level. If a low level output is produced by the sensor, the valve is opened to allow water to flow from the tank to the reservoir. If the valve remains open for longer than a predetermined time without the sensor indicating a full level, the autoclave produces a fault signal.

5 Claims, 1 Drawing Sheet

AUTOCLAVES

BACKGROUND OF THE INVENTION

This invention relates to autoclaves.

Autoclaves are used for sterilization or other treatment of articles at elevated temperature in the presence of liquid vapor at elevated pressure. The articles to be treated are placed in a pressure vessel which includes a heater and a reservoir of liquid such as distilled water. In operation, the vessel is closed and the heater turned on so that the water is heated. The steam produced is allowed to vent from the vessel for a short time so as to flush air from the apparatus. The air vent is then closed so that pressure and temperature within the vessel increase to predefined levels. The atmosphere of high humidity and temperature in the vessel is sufficient to sterilize the articles after a predetermined time. When the sterilization cycle is complete, the heater is turned off and the vessel is allowed to cool, or is actively cooled such as by a fan. When the pressure in the vessel has dropped to a safe level, the door of the vessel is unlocked allowing the articles to be removed and other articles to be sterilized. Each cycle results in a loss of some of the water or other liquid in the vessel which must be replaced. This is generally achieved automatically by supply from a tank outside the pressure vessel at the start of a new cycle. A level sensor in the vessel reservoir detects when there is sufficient liquid present so as to prevent overfilling. Overfilling can be dangerous since, in some cases, it could result in hot water flooding out of the vessel door when this is opened at the end of the cycle.

Because of the adverse environment within the pressure vessel caused by the high pressure and temperature, the liquid level sensor used must be of a robust construction. Generally, the only form of sensor suitable for such an application is a conductivity sensor which detects the presence of a liquid by its effect on reducing the electrical resistance between two electrodes. One problem, however, with this form of sensor is that liquid may cling to it even when not actually immersed in the liquid so that it gives a false indication of the presence of liquid.

BRIEF SUMMARY OF THE INVENTION

It is an object of the present invention to provide an autoclave that can be used to avoid the above-mentioned problem.

According to one aspect of the present invention there is provided an autoclave having a pressure vessel, a liquid reservoir opening into the pressure vessel, and a liquid level sensor arranged to provide an indication of the level of liquid in the reservoir, means for heating liquid in the reservoir, a tank external of the pressure vessel containing liquid for supply to the reservoir, means for detecting whether the sensor indicates a full or low level of liquid, means for supplying liquid from the tank to the reservoir in response to an indication of a low level of liquid in the reservoir, the autoclave including means for heating the liquid level sensor in response to an indication of a full level of liquid in the reservoir to drive off liquid clinging to any part of the sensor not immersed in the liquid, and the autoclave being arranged subsequently either to commence a pressure cycle if the sensor indicates a full level of liquid in the reservoir or to supply liquid from the tank to the reservoir if the sensor continues to indicates a low level of liquid in the reservoir.

The means for heating the sensor is preferably the means for heating liquid in the reservoir. The means for heating liquid in the reservoir may be an electrical resistance heater. Where the liquid is electrically conductive, the liquid level sensor is preferably a conductivity sensor. The autoclave may include an electrically-operated valve connected between the reservoir and the tank, the liquid being supplied from the tank to the reservoir by opening the valve.

According to another aspect of the present invention there is provided a method of operating an autoclave of the kind having a pressure vessel, a liquid reservoir opening into the pressure vessel, and a liquid level sensor arranged to provide an indication of the level of liquid in the reservoir, including the steps of: checking if the sensor indicates a low level of liquid and supplying liquid to the reservoir in response thereto, checking if the sensor indicates a full level of liquid and causing the sensor to be heated in response thereto so as to drive off any liquid clinging to any part of the sensor not immersed in the liquid, checking whether the sensor continues to indicate a full level of liquid, and subsequently either initiating a pressure cycle in response to a full level indication or supplying liquid to the reservoir in response to a low level indication.

The sensor may be heated again in response to the sensor continuing to indicate a full level of liquid prior to the subsequent step of initiating a pressure cycle or supplying liquid to the reservoir. The pressure cycle initiated by the subsequent step, following repeated heating of the sensor and the sensor continuing to indicate a full level of liquid, may be a trial cycle during which the pressure and temperature of the vessel are monitored for any departure from normal behavior. If the sensor indicates a low level of liquid, a valve is opened to allow liquid to flow from the tank to the reservoir until the sensor indicates a full level of liquid. If the sensor indicates a low level of liquid and a valve is opened to allow liquid to flow from the tank to the reservoir, if the sensor does not indicate a full level of liquid within a predetermined time a fault indication may be produced.

An autoclave for use in sterilization will now be described, by way of example, with reference to the accompanying drawings.

DESCRIPTION OF THE PREFERRED EMBODIMENTS

Figure 1:
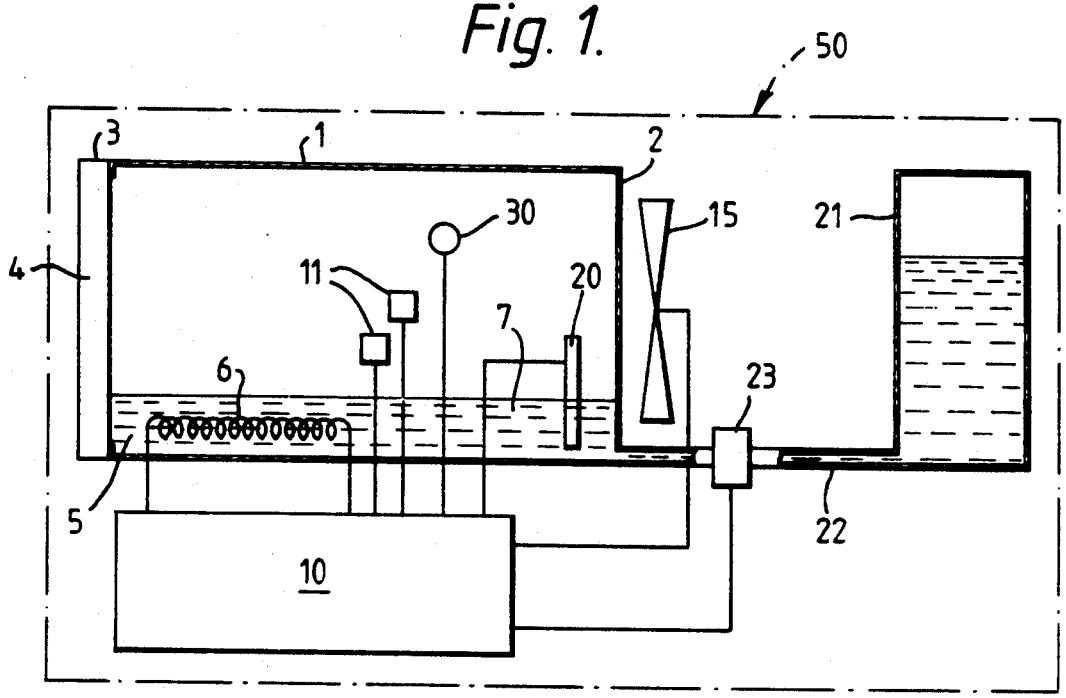
FIG. 1 is a schematic side elevation view of the autoclave.

With reference first to FIG. 1, the autoclave sterilizer comprises a cylindrical pressure vessel 1 that is closed at its rear end 2 and open at its front end 3. A door 4 is provided at the front end 3 which can be closed to seal the vessel 1 after insertion of the articles to be sterilized. The lower part of the vessel 1 provides a water reservoir 5 in which is located an electrical resistance heating filament 6 that is immersed in water 7. Current can be supplied to the filament 6 from a control unit 10. The reservoir 5 need not be within the pressure vessel 1 itself providing it opens into the pressure vessel.

A water level sensor 20 is mounted in the water reservoir 5 to indicate the level of water in the reservoir. The sensor 20 is of the conductivity kind having two electrodes exposed to any water in which the sensor is immersed. In this way, the resistance between the two electrodes falls when the level of conductive water reaches its full level and rises when the electrodes are exposed by a fall in the water level below the full level. An output from the sensor 20 is supplied to the control unit 10.

The sterilizer also includes a tank 21 external of the pressure vessel 1 which is connected with the reservoir 5 via tubing 22 and an electrically-operated valve 23. The valve 23 is controlled by the control unit 10 which also receives input signals from various sensors 11 in accordance with, for example, temperature and pressure.

Projecting through the wall of the vessel 1 there is a valve 30 which allows escape of air but shuts to allow a build up of pressure.

A cooling fan 15 is mounted outside the rear of the pressure vessel 1 and arranged to blow air onto the vessel 1 to promote cooling at the end of the sterilizing cycle. The pressure vessel 1 is contained within an outer housing 50 which is insulated from the pressure vessel 1 and which supports the various control switches and display panels, not shown.

In operation, articles to be sterilized are placed within the pressure vessel 1, the door 4 is closed and the sterilizer is turned on. This causes the water level sensor 20 to be checked by the control unit 10. If the control unit 10 sees a high resistance at the sensor 20 this indicates that the level of water in the reservoir 5 is low and thereby causes the control unit to open the valve 23 and allow water from the tank 21 to flow along the tubing 22 into the reservoir 5. This continues until the sensor 20 gives a full level output. If no full level output is produced by the sensor 20 after a predetermined time, a fault is indicated by the unit 10 to show either that the tank 21 is empty or that the level sensor 20 is faulty.

Once the output of the sensor 20 has changed from a low to a full level output, the valve 23 is closed and the sterlizing/pressure cycle is started.

If, however, when the sterilizer is turned on, the output of the sensor 20 indicates a full level, a different sequence of operation is initiated. A full output from the sensor 20 may indicate either that the operative part of the sensor is immersed in water in the reservoir 5 and that the reservoir is therefore full, or that the operative part of the sensor is exposed above the level of water in the reservoir but that the operative part is wet as a result of water clinging to the sensor from the previous cycle. The reservoir will normally need to be filled at the start of a cycle because water will have been lost during the preceding cycle. A full output from the sensor at the start of the cycle, therefore, is generally indicative of an exposed but wet sensor. It will be appreciated that if this full output is simply interpreted as an indication that the reservoir contains the correct amount of water, the sterilization cycle will be started with insufficient water. This will usually lead to the cycle aborting because of failure to reach the correct pressure and can result in damage to the heater 6. On the other hand, if the sensor output is ignored and the reservoir is automatically filled from the tank with extra water, this can lead to overfilling with the consequent danger that hot water will flood out the vessel 1 when the door 4 is opened.

The present invention reduces this risk by causing the heater 6 to be energized to warm the pressure vessel 1 and, more particularly, to warm the sensor 20 for a predetermined time. The amount of heating produced is less than during a normal pressure cycle, so that it is insufficient to cause damage if the heater 6 is exposed above the water, but is sufficient to promote drying of the sensor or any part of the sensor exposed above the water level. During this period, the valve 30 is open so that water evaporated from the sensor can escape. After the predetermined time, the output of the sensor 20 is rechecked by the control unit 10. If the output now indicates that there is a low water level, the valve 23 is opened to allow water from the tank 21 into the reservoir 5 in the manner described above. If, however, the output from the sensor 20 still indicates a high water level, the heater 6 is either reenergized or maintained energized for another predetermined period after which the output of the sensor 20 is rechecked again. This may be repeated several times after which, if the sensor still produces a full level output, a trial sterilization cycle is started. During this cycle, the pressure and temperature in the vessel 1 are monitored closely for any departure from normal behavior. If the cycle operates normally, it is continued as a full sterilization cycle. If some anomalous behavior is observed, the autoclave reverts to a safe state in which the heater is turned off, the door is maintained locked and a valve (not shown) is opened to exhaust pressure in the vessel 1 such as to the water tank 21.

In this way, the risk of the autoclave operating with insufficient water is minimized.

To ensure that articles are correctly sterilized it is important to ensure that they are maintained at a sufficiently high temperature and pressure for sufficient time. It is now a requirement in some countries that the timing of the sterilizing phase of operation of the autoclave be verified by a clock which is separate from the clock used for timing other routine timing functions in the autoclave. Examples of such routine timing functions are: the time control for the heater to dry the chamber water level sensor, the timing of the valve 23 being open, the timing of an initial heating phase to determine if the heater is functioning correctly, the timing of the drying cycle, and timing routines for the autoclave display, i.e., the frequency of flashing characters on the display.

Figure 2:
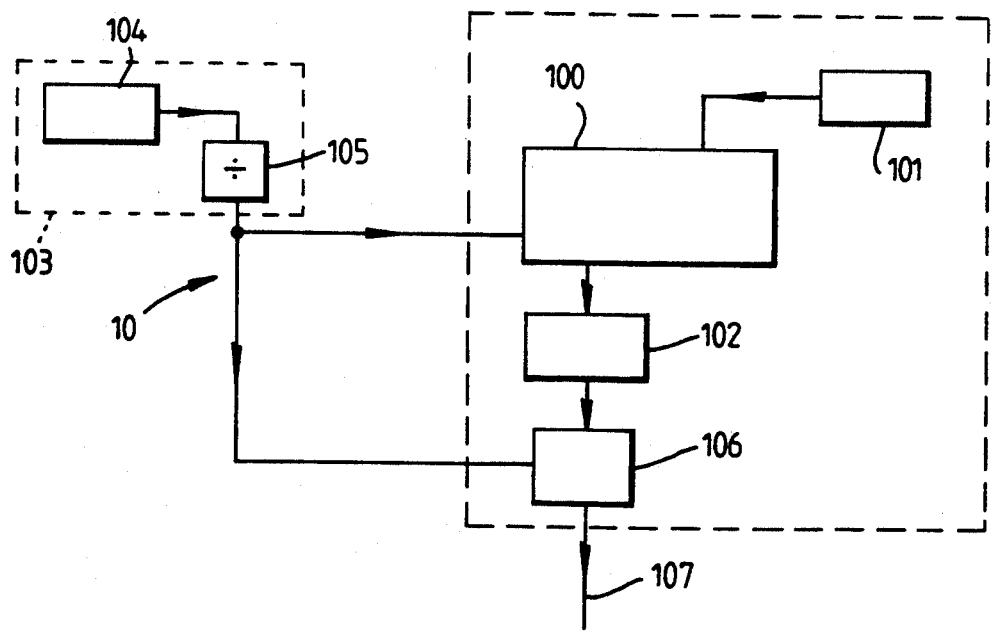
FIG. 2 illustrates operation of a part of the autoclave.

With reference to FIG. 2, the control unit 10 of the autoclave includes a 128 bytes RAM type 6802 microprocessor 100 having its own clock 101 derived from a 3.2768 MHz crystal. The software of the microprocessor 100 counts the number of times that a certain portion of the program is executed. The portion of the program which is counted is one which is only performed during the pressurization/sterilization phase, which is the only time during which dual timing is needed. In this particular example, it is a proportional temperature control algorithm which is counted but other portions of the program which are performed during the pressurization phase could alternatively be counted. This count is directly related to the frequency of the clock 101 and the duration of the pressurization period. The portion of the program counted takes approximately 0.8 s to perform, thus, for a standard 134° C. cycle taking 200 s, the count would be approximately 250. The expected number of counts for a correct duration period, i.e. 250, is separately established and entered in a register 102 before the start of the pressurization period and this number is reduced by one each time that the relevant portion of the program is executed.

The control unit 10 also includes a separate oscillator 103 having a crystal 104 running at 32.768 KHz which produces a fundamental divided frequency of 200 Hz. The oscillator 103 is used to control the pressurization/sterilization cycle time by dividing a fundamental frequency at divider 105 to produce accurate 0.5 s intervals. The output from divider 105 is supplied to the microprocessor 100, for use in timing the sterilization phase. At the end of the pressurization phase, a comparator 106 is triggered to check that the contents of the register 102 reads 0 to within a predetermined allowable error. If the contents of the register 102 differs by more than a predetermined amount from this 0 reading, a fault indication is produced in the form of an output on line 107. This causes an indication to be produced on a visual display (not shown) and causes the autoclave to revert to a safe state. More particularly, the door lock of the autoclave is maintained closed to prevent access to the articles in the autoclave which will not have been fully sterilized. Various other, similar ways of timing the operation of the autoclave are possible. For example, the count of the number of times the portion of the program is executed could be entered in one register and the separately established count representative of the desired duration of the pressurization period entered in a different register. At the end of the pressurization period, as controlled by the oscillator 103, the contents of the two registers would be checked and a fault indication provided if they differ by more than a predetermined amount.

What I claim is:

1. A method of operating an autoclave of the kind having a pressure vessel, a liquid reservoir opening into the pressure vessel and a liquid level sensor that provides an output indication of the level of the liquid in the reservoir, comprising the steps of: either (a) supplying liquid to the reservoir in response to an output from the sensor indicative that the level of liquid is below a predetermined level and subsequently initiating a pressure cycle in response to an output from the sensor indicative that the level of liquid is above said predetermined level; or (b) causing the sensor to be heated in response to an output from the sensor indicative that the level of liquid is above said predetermined level so as to drive off any liquid clinging to any part of the sensor not immersed in the liquid, checking whether the sensor continues to indicate that the level of liquid is above said predetermined level, and subsequently either initiating a pressure cycle in response to an indication that the level of liquid is above said predetermined level or supplying liquid to the reservoir in response to an indication that the level of liquid is below said predetermined level.

2. A method according to claim 1, including the additional step of reheating the sensor in response to the sensor continuing to indicate that the level of liquid is above said predetermined level prior to the subsequent step of initiating a pressure cycle or supplying liquid to the reservoir.

3. A method according to claim 2, wherein the pressure and temperature of the vessel are monitored during the pressure cycle initiated by said subsequent step, following repeated heating of the sensor, and wherein any departure from a predetermined behavior is signalled.

4. A method according to claim 1 wherein, if the sensor indicates that the level of liquid is below said predetermined level, a valve is opened to allow liquid to flow from the tank to the reservoir, and wherein if the sensor does not indicate that the level of liquid is above said predetermined level within a predetermined time following opening of the valve, a fault indication is produced.

5. A method of operating an autoclave of the kind having a pressure vessel, a liquid reservoir opening into the pressure vessel, a heater in the reservoir that heats liquid in the reservoir, a tank of liquid connected to the reservoir by an electrically-operated valve, and a liquid level sensor that provides an output indicative of the level of liquid in the reservoir, comprising the steps of: at the start of an operation cycle, either (a) opening the valve to allow liquid in the tank to flow to the reservoir in response to the output of the sensor indicating that the level of liquid is below a predetermined level, and subsequently initiating a pressure cycle; or (b) heating the sensor for a predetermined time in response to the output of the sensor indicating that the level of liquid is above said predetermined level so as to drive off any liquid clinging to any part of the senor not immersed in the liquid and, after said predetermined time, monitoring the output of the sensor, and subsequently either initiating a pressure cycle in response to the output of the sensor then indicating that the level of liquid is above said predetermined level or opening the valve to allow liquid in the tank to flow to the reservoir in response to the output of the sensor then indicating that the level of liquid is below said predetermined level.

* * * * *